US00PP27996P3

(12) United States Plant Patent
Grazzini

(10) Patent No.: US PP27,996 P3
(45) Date of Patent: May 9, 2017

(54) ***PELARGONIUM* PLANT NAMED 'G12120'**

(50) Latin Name: ***Pelargonium×hortorum×Pelargonium* sp.**
Varietal Denomination: G12120

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 117 days.

(21) Appl. No.: 14/545,630

(22) Filed: May 29, 2015

(65) Prior Publication Data

US 2016/0353643 P1 Dec. 1, 2016

(51) Int. Cl.
*A01H 5/02* (2006.01)

(52) U.S. Cl.
USPC ..... Plt./330

(58) Field of Classification Search
USPC ..... Plt./263.1, 324, 325, 330
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of interspecific *Pelargonium* plant named 'G12120', characterized by its upright and uniformly mounding to trailing plant habit; vigorous growth habit; freely branching habit; green and white variegated leaves; light scarlet-colored flowers; and good garden performance.

1 Drawing Sheet

Botanical designation: *Pelargonium×hortorum×Pelargonium* sp.
Cultivar denomination: 'G12120'.

BACKGROUND OF THE INVENTION

The present invention relates to a new and distinct cultivar of interspecific Geranium plant, botanically known as *Pelargonium×hortorum×Pelargonium* sp., and hereinafter referred to by the name 'G12120'.

The new interspecific *Pelargonium* plant is a product of a planned breeding program conducted by the Inventor in Bellefonte, Pa. The objective of the breeding program is to create new vigorous interspecific *Pelargonium* plants with attractive leaf and flower coloration and good high light and high temperature tolerance.

The new interspecific *Pelargonium* plant originated from a cross-pollination made by the Inventor in Bellefonte, Pa. on Aug. 15, 2011 of *Pelargonium×hortorum* 'Catalina', not patented, as the female, or seed, parent with a proprietary seedling selection of *Pelargonium* sp. identified as code number 7875, not patented, as the male, or pollen, parent. The new interspecific *Pelargonium* plant was discovered and selected by the Inventor as a flowering plant from within the progeny of the stated cross-pollination in a controlled environment in Bellefonte, Pa. on May 15, 2012.

Asexual reproduction of the new interspecific *Pelargonium* plant by vegetative terminal cuttings in a controlled environment in Bellefonte, Pa. since Aug. 15, 2012, has shown that the unique features of this new interspecific *Pelargonium* plant are stable and reproduced true to type in successive generations.

SUMMARY OF THE INVENTION

Plants of the new interspecific *Pelargonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G12120'. These characteristics in combination distinguish 'G12120' as a new and distinct interspecific *Pelargonium* plant:

1. Upright and uniformly mounding to trailing plant habit.
2. Vigorous growth habit.
3. Freely branching habit.
4. Green and white variegated leaves.
5. Light scarlet-colored flowers.
6. Good garden performance.

Plants of the new interspecific *Pelargonium* differ primarily from plants of the female parent, 'Catalina', in the following characteristics:

1. Plants of the new interspecific *Pelargonium* are more trailing than and not as upright as plants of 'Catalina'.
2. Plants of the new interspecific *Pelargonium* are more freely branching than plants of 'Catalina'.
3. Leaves of plants of the new interspecific *Pelargonium* are reniform to palmate in shape whereas leaves of plants of 'Catalina' are orbicular in shape.
4. Plants of the new interspecific *Pelargonium* have smaller flowers than plants of 'Catalina'.
5. Plants of the new interspecific *Pelargonium* and 'Catalina' differ in flower color as plants of 'Catalina' have bright pink-colored flowers.

Plants of the new interspecific *Pelargonium* differ primarily from plants of the male parent selection in the following characteristics:

1. Plants of the new interspecific *Pelargonium* are more freely branching than plants of the male parent selection.

2. Plants of the new interspecific *Pelargonium* have thicker stems than plants of the male parent selection.
3. Leaves of plants of the new interspecific *Pelargonium* are variegated whereas leaves of plants of the male parent selection are not variegated (solid green in color).
4. Plants of the new interspecific *Pelargonium* have larger flowers than plants of the male parent selection.

Plants of the new interspecific *Pelargonium* can be compared to plants of the *Pelargonium×hortorum* 'Wilhelm Langguth', not patented. In side-by-side comparisons conducted in Bellefonte, Pa., plants of the new interspecific *Pelargonium* differed from plants of 'Wilhelm Langguth' in the following characteristics:

1. Plants of the new interspecific *Pelargonium* were more compact than plants of 'Wilhelm Langguth'.
2. Plants of the new interspecific *Pelargonium* were more mounding and trailing than and not as upright as plants of 'Wilhelm Langguth'.
3. Plants of the new interspecific *Pelargonium* were more freely branching and denser than plants of 'Wilhelm Langguth'.
4. Leaves of plants of the new interspecific *Pelargonium* are reniform to palmate in shape whereas leaves of plants of 'Wilhelm Langguth' are orbicular in shape.
5. Plants of the new interspecific *Pelargonium* had smaller flowers than plants of 'Wilhelm Langguth'.
6. Plants of the new interspecific *Pelargonium* and 'Wilhelm Langguth' differed in flower color as plants of 'Wilhelm Langguth' had dark scarlet-colored flowers.

Plants of the new interspecific *Pelargonium* can also be compared to plants of the *Pelargonium×hortorum* 'Crystal Palace', not patented. In side-by-side comparisons conducted in Bellefonte, Pa., plants of the new interspecific *Pelargonium* differed from plants of 'Crystal Palace' in the following characteristics:

1. Plants of the new interspecific *Pelargonium* were more compact than plants of 'Crystal Palace'.
2. Plants of the new interspecific *Pelargonium* were more freely branching and denser than plants of 'Crystal Palace'.
3. Leaves of plants of the new interspecific *Pelargonium* are reniform to palmate in shape whereas leaves of plants of 'Crystal Palace' are orbicular in shape.
4. Plants of the new interspecific *Pelargonium* and 'Crystal Palace' differed in leaf color as plants of 'Crystal Palace' have green and golden yellow variegated leaves.
5. Plants of the new interspecific *Pelargonium* and 'Crystal Palace' differed in flower color as plants of 'Crystal Palace' had dark scarlet-colored flowers.

BRIEF DESCRIPTION OF THE PHOTOGRAPHS

The accompanying colored photographs illustrate the overall appearance of the new interspecific *Pelargonium* plant showing the colors as true as it is reasonably possible to obtain in colored reproductions of this type. Colors in the photographs may differ slightly from the color values cited in the detailed botanical description which accurately describe the colors of the new interspecific *Pelargonium* plant.

The photograph at the bottom of the sheet is a side perspective view of a typical flowering plant of 'G12120' grown in a container.

The photograph at the top of the sheet is a close-up view of a typical flowering plants of 'G12120' grown in a container.

DETAILED BOTANICAL DESCRIPTION

The aforementioned photographs and following observations, measurements and values describe plants grown during the early spring in 11.5-cm containers in a polycarbonate-covered greenhouse in Bellefonte, Pa. and under cultural practices which closely approximate commercial production. During the production of the plants, day temperatures ranged from 16° C. to 24° C. and night temperatures ranged from 10° C. to 16° C. Plants were pinched one time and were 14 weeks old when the photographs and description were taken. In the detailed description, color references are made to The Royal Horticultural Society Colour Chart, 2007 Edition, except where general terms of ordinary dictionary significance are used.

Botanical classification: *Pelargonium×hortorum×Pelargonium* sp. 'G12120'.

Parentage:

*Female, or seed, parent.*—*Pelargonium×hortorum* 'Catalina', not patented.

*Male or pollen parent.*—Proprietary seedling selection of *Pelargonium* sp. identified as code number 7875, not patented.

Propagation:

*Type.*—By vegetative terminal cuttings.

*Time to initiate roots, summer.*—About 10 to 14 days at temperatures about 22° C.

*Time to initiate roots, winter.*—About 14 to 21 days at temperatures about 22° C.

*Time to produce a rooted young plant, summer.*—About 56 days at temperatures about 22° C.

*Time to produce a rooted young plant, winter.*—About 70 days at temperatures about 22° C.

*Root description.*—Medium in thickness, fibrous; white to tan in color.

*Rooting habit.*—Moderately freely branching; medium density.

Plant description:

*Plant and growth habit.*—Upright and uniformly mounding to trailing plant habit; densely foliated; vigorous growth habit; freely basal branching habit with about six primary lateral branches developing per plant.

*Plant height, to top of umbels.*—About 16 cm.

*Plant height, to top of leaves.*—About 8.8 cm.

*Plant width.*—About 18 cm.

*Lateral branches.*—Length: About 5.7 cm. Diameter: About 5 mm. Internode length: About 6 mm. Strength: Strong. Aspect: Upright to outwardly spreading; more trailing with development. Texture: Pubescent. Color: Close to 144C.

Leaf description:

*Arrangement.*—Alternate and whorled; simple.

*Length.*—About 4.3 cm.

*Width.*—About 5.7 cm.

*Shape.*—Reniform to palmate.

*Apex.*—Rounded.

*Base.*—Cordate.

*Margin.*—Shallow palmate lobes with shallow crenations.

*Venation pattern*.—Palmate.

*Texture, upper and lower surfaces*.—Pubescent, soft; rugose.

*Color*.—Developing leaves, upper surface: Close to 143A; towards the margins, close to 155A. Developing leaves, upper surface: Close to 147B; towards the margins, close to NN155B. Fully expanded leaves, upper surface: Close to N137B; towards the margins, close to 155C; venation, close to 147B. Fully expanded leaves, upper surface: Close to N138C; towards the margins, close to 155C; venation, close to 147C.

*Zonation pattern*.—Not discernible.

*Petioles*.—Length: About 6 cm. Diameter: About 2 mm. Texture, upper and lower surfaces: Pubescent; soft. Color, upper and lower surfaces: Close to 147B.

Flower description:

*Flower arrangement*.—Single-type flowers arranged in rounded hemispherical umbels arising from apical leaf axils; umbels displayed above the foliar plane on strong peduncles; flowers mostly flat and face upright to outward depending on the position in the umbel.

*Fragrance*.—None detected.

*Quantity of flowers*.—About four umbels in flower at a time per plant; each umbel with about 20 flower buds and open flowers.

*Flowering season*.—Early flowering habit, plants begin flowering about six to eight weeks after planting; in the greenhouse, plants flower year-round; in the garden in Pennsylvania, flowering is continuous from April until frost in the autumn.

*Flower longevity*.—Individual flowers last about three to four days on the plant; umbels last about two to three weeks on the plant; flowers not persistent.

*Umbel height*.—About 2.8 cm.

*Umbel diameter*.—About 3.8 cm.

*Flower diameter*.—About 2.2 cm.

*Flower depth* (*height*).—About 7 mm.

*Flower buds*.—Length: About 1.2 cm. Diameter: About 5 mm. Shape: Ovoid. Color: Close to 187D.

*Petals*.—Quantity and arrangement: Five per flower arranged in a single whorl; petals imbricate. Length, upper and lower petals: About 1.2 cm. Width, upper and lower petals: About 7 mm. Shape: Obovate. Apex: Rounded. Base: Attenuate. Margin: Entire. Texture, upper and lower surfaces: Smooth, glabrous. Color: When opening, upper surface: Close to 46B. When opening, lower surface: Close to 53D. Fully opened, upper surface: Close to 42A; venation, close to 42A; color becoming closer to 44A with development. Fully opened, lower surface: Close to 42C; venation, close to 42C; color becoming closer to 44B with development.

*Petaloids*.—None observed.

*Sepals*.—Quantity and arrangement: Five per flower arranged in a single whorl. Length: About 6 mm. Width: About 2.5 mm. Shape: Lanceolate. Apex: Acute. Base: Truncate. Margin: Entire. Texture, upper surface: Smooth, glabrous. Texture, lower surface: Slightly pubescent, minute. Color, upper and lower surfaces: Close to 146B; towards the margins, close to 155B.

*Peduncle* (*umbel stem*).—Length: About 13.7 cm. Diameter: About 2 mm. Strength: Strong. Aspect: About 30° from stem axis. Texture: Pubescent, minute. Color: Close to 146B.

*Pedicel* (*individual flower stem*).—Length: About 1.1 cm. Diameter: About 1 mm. Strength: Strong; flexible. Aspect: Variable depending on position within the umbel. Texture: Pubescent, minute. Color: Close to 146B.

*Reproductive organs*.—Androecium: Quantity of stamens: About five to ten per flower. Filament length: About 2 mm. Filament color: Close to NN155A. Anther length: About 1.5 mm. Anther shape: Oval. Anther color: Close to 70D. Pollen amount: Scarce. Pollen color: Close to 164B. Gynoecium: Quantity of pistils: One per flower. Pistil length: About 5 mm. Stigma shape: Five-parted. Stigma color: Close to 53A. Style length: About 1 mm. Style color: Close to 53A. Ovary color: Close to 195C. Seeds: Seed development has not been observed on plants of the new interspecific *Pelargonium*.

Disease & pest resistance: Plants of the new interspecific *Pelargonium* have been observed to be resistant to *Botrytis*. Plants of the new interspecific *Pelargonium* have not been observed to be resistant to pests and other pathogens common to *Pelargonium* plants.

Garden performance: Plants of the new interspecific *Pelargonium* have been observed to have good garden performance and to tolerate rain, wind, high light conditions and temperatures ranging from about 1° C. to about 35° C.

It is claimed:

1. A new and distinct interspecific *Pelargonium* plant named 'G12120' as illustrated and described.

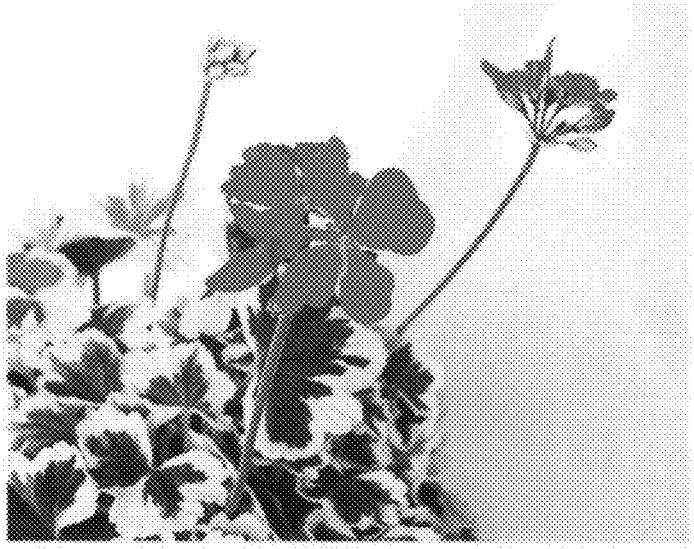
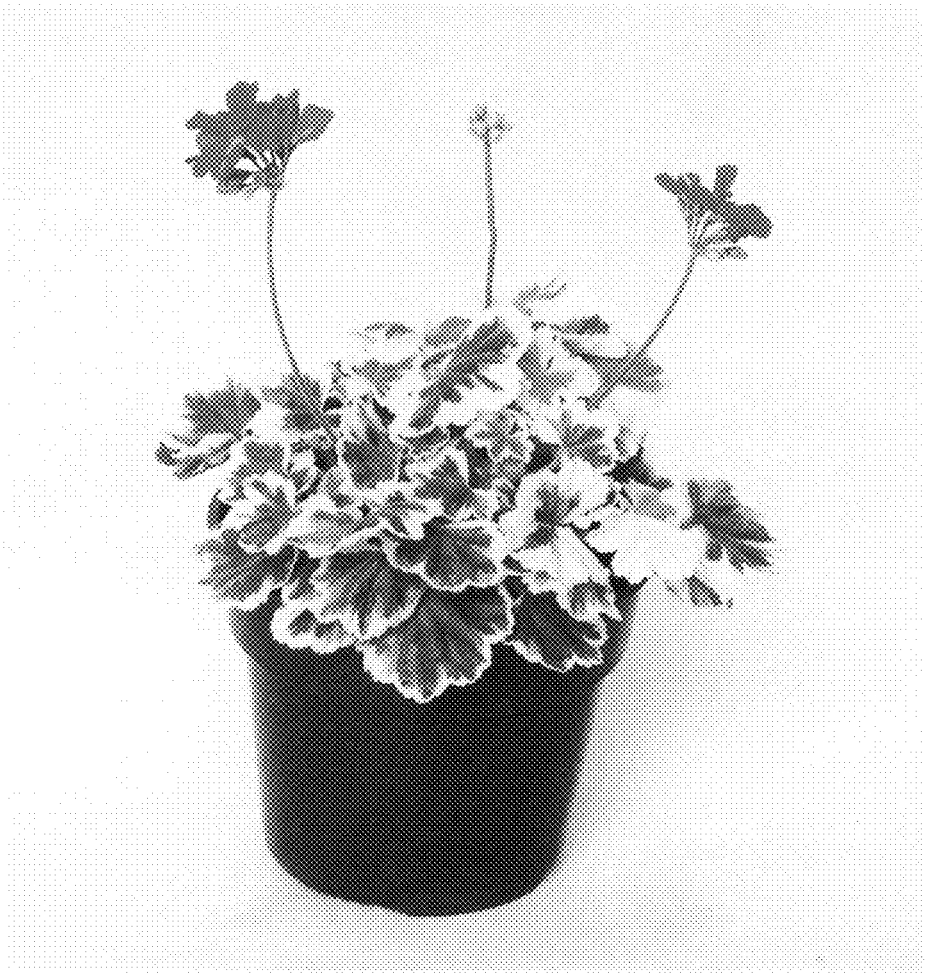

* * * * *